US 7,597,680 B2

(12) United States Patent
Watanabe et al.

(10) Patent No.: US 7,597,680 B2
(45) Date of Patent: Oct. 6, 2009

(54) SYRINGE DEVICE AND METHOD OF PREPARING MEDICINE USING THE DEVICE

(75) Inventors: Norio Watanabe, Fujieda (JP); Yasuhiko Sato, Fujieda (JP); Kouichi Sugita, Osaka (JP); Katsuya Taguchi, Osaka (JP)

(73) Assignee: Kaken Pharmaceutical Co., Ltd., Bunkyo-Ku, Tokyo (JP)

( * ) Notice: Subject to any disclaimer, the term of this patent is extended or adjusted under 35 U.S.C. 154(b) by 139 days.

(21) Appl. No.: 11/883,934

(22) PCT Filed: Feb. 8, 2006

(86) PCT No.: PCT/JP2006/302155
§ 371 (c)(1),
(2), (4) Date: Oct. 3, 2007

(87) PCT Pub. No.: WO2006/085546

PCT Pub. Date: Aug. 17, 2006

(65) Prior Publication Data
US 2008/0177226 A1     Jul. 24, 2008

(30) Foreign Application Priority Data
Feb. 9, 2005   (JP) .............................. 2005-033218

(51) Int. Cl.
A61M 37/00   (2006.01)
A61M 39/00   (2006.01)
A61M 39/10   (2006.01)
A61M 25/16   (2006.01)
A61M 25/18   (2006.01)

(52) U.S. Cl. ............................ 604/82; 604/92; 604/89; 604/90; 604/905; 604/533

(58) Field of Classification Search .................. 604/92, 604/82–83, 89–90, 187, 533–536, 905; 366/241, 366/268
See application file for complete search history.

(56) References Cited

U.S. PATENT DOCUMENTS 3,872,867 A * 3/1975 Killinger ..................... 604/413

(Continued)

FOREIGN PATENT DOCUMENTS

EP        0 266 058 A2   5/1988

(Continued)

OTHER PUBLICATIONS

International Search Report dated May 1, 2006.

*Primary Examiner*—Nicholas D Lucchesi
*Assistant Examiner*—Rebecca E Eisenberg
(74) *Attorney, Agent, or Firm*—Buchanan Ingersoll & Rooney PC

(57) ABSTRACT

A syringe device and a method of preparing medicine using the device capable of easily and accurately performing operations for mixing and dissolving a lyophilized product into a dissolution liquid before use. A double ended needle assembly and an intermediate holder are fitted to the first cylindrical part of a connection holder, a first syringe in which the dissolution liquid is stored is inserted into the first cylindrical part through the intermediate holder, and a second syringe in which the lyophilized product is stored in a depressurized state is fixedly inserted into the second cylindrical part of the connection holder. First, the intermediate holder is locked by a finger hooking projected piece, the first syringe is pushed into the intermediate holder in the locked state of the double ended needle assembly at an initial position by locking ribs, and the first syringe is unsealed by one end of the double ended needle. Next, the intermediate holder and the double ended needle assembly are pushed into the first cylindrical part by the first syringe, and the second syringe in the second cylindrical part is unsealed by the other end of the double ended needle.

4 Claims, 16 Drawing Sheets

U.S. PATENT DOCUMENTS

| | | | |
|---|---|---|---|
| 5,334,162 A * | 8/1994 | Harris | 604/232 |
| 5,445,631 A * | 8/1995 | Uchida | 604/412 |
| 5,566,729 A * | 10/1996 | Grabenkort et al. | 141/25 |
| 6,752,180 B2 * | 6/2004 | Delay | 141/97 |
| 2003/0069538 A1 * | 4/2003 | Pfeifer et al. | 604/82 |

FOREIGN PATENT DOCUMENTS

| | | |
|---|---|---|
| JP | 63-277060 A | 11/1988 |
| JP | 11-155951 A | 6/1999 |
| JP | 2001-505072 A | 4/2001 |
| JP | 2003-518411 A | 6/2003 |
| WO | 97/46202 A1 | 12/1997 |
| WO | 01/47571 A2 | 7/2001 |

* cited by examiner

SYRINGE DEVICE AND METHOD OF PREPARING MEDICINE USING THE DEVICE

TECHNICAL FIELD

The present invention relates to a syringe device, in which a solution is mixed with a soluble pharmaceutical drug, to be used in a dissolved state before use, and a method of preparing liquids and solutions using the device. More particularly, the present invention relates to a syringe device, in which a solid lyophilized product or a powdery agent is principally used as a soluble pharmaceutical drug, and a method of preparing liquids and solutions using the device.

BACKGROUND ART

Conventionally, a lyophilized product, for example, is dissolved before use, and then, is given to a person. However, some lyophilized products are unstable since they are liable to be dissolved in water, oxygen or the like, or have bubbles which are hardly dissipated during dissolution. The lyophilized products such as an antibiotic, a growth hormone or a vaccine are stably stored or generally stored in a vial under a reduced pressure lower than an atmospheric pressure in order to prevent any generation of bubbles during the dissolution. However, in the case where the lyophilized product is stored in the vial, a dissolved liquid medicine need be transferred into a syringe, and therefore, it cannot be used at once. Otherwise, in the case where the liquid medicine obtained by dissolving the lyophilized product has a high viscosity, the syringe hardly sucks up the liquid medicine.

To deal with the above mentioned problem, as shown in FIG. 18 (see Patent Document 1), the inventors of the present application have developed a pressure reducing syringe 102 capable of storing a lyophilized product M therein under a reduced pressure by utilizing a sealed rubber plug 100 with a flange and a piston (i.e., a gasket) 101 having an air-liquid relief groove. In using the pressure reducing syringe 102 shown in FIG. 18, an outside syringe 105 having a syringe needle 103 attached thereto is prepared independently of the pressure reducing syringe 102. In this state, the syringe needle 103 of the outside syringe 105 pierces a rubber plug 108 of a vial 107 containing an attached solvent L therein. And then, a tip rubber packing 112 fixed to the pressure reducing syringe 102 is unsealed by one end (i.e., an upper end) of the syringe needle 103 by inserting the pressure reducing syringe 102 into the outside syringe 105, as indicated by an arrow. Subsequently, the sealed rubber plug 100 of the pressure reducing syringe 102 is detached, and further, a push rod 111 is connected to the piston 101, as shown in FIG. 19. Finally, the attached solvent L is sucked up into the pressure reducing syringe 102, to be dissolved inside of the syringe 102.

Patent Document 1: Japanese Patent Application Laid-open No. 11-155951

DISCLOSURE OF THE INVENTION

Problems to be Solved by the Invention

However, in the case where the attached solvent L contained inside of the vial 107 is sucked up as shown in FIG. 19, the syringe needle 103 of the outside syringe 105 need pierce in the state in which the vial 107 is fixed by any means, and further, the attached solvent L need be sucked up by a predetermined quantity while visually measuring a suction quantity. This takes much labor and time in mixture and dissolution before use, and therefore, experience and skill are required to operate with speed and accuracy.

Object of the Invention

An object of the present invention is to provide a syringe device, in which a predetermined quantity of solution can be readily mixed with and dissolved in a predetermined quantity of soluble pharmaceutical drug such as a lyophilized product with accuracy in a good state without either experience or skill before use.

Means for Solving the Problems

In order to solve the above-described problems, a syringe device according to claim 1 of the present invention comprises: a cylindrical connection holder 6 which is partitioned into a first cylindrical part 11 and a second cylindrical part 12 via a partition wall 31 having a through hole 30 formed thereat; a cylindrical and bottomed intermediate holder 3 having a needle inserting hole 46 formed at a tip of a bottom thereof; a first cylindrical and bottomed syringe 1 which contains a solution therein and is unsealably sealed at a tip of a bottom thereof; a second cylindrical and bottomed syringe 2 which contains a soluble pharmaceutical drug therein and is unsealably sealed at a tip of a bottom thereof, and a double ended needle assembly 10; the double ended needle assembly 10 and the intermediate holder 3 being inserted in this order into the first cylindrical part 11, the first syringe 1 being inserted into the intermediate holder 3, and the second syringe 2 being inserted into the second cylindrical part 12; wherein the double ended needle assembly 10 is locked at an initial position, at which a needle sharp tip 55*a* on a side of the partition wall 31 cannot project inward of the second cylindrical part 12 by a locking portion, and further, can be moved against a frictional resistance of the locking portion from the initial position to a second position, at which the needle sharp tip 55*a* passes through the through hole 30 so as to unseal the tip of the bottom of the second syringe 2; and the intermediate holder 3 is locked at a standby position, at which it cannot act on the double ended needle assembly 10 at the initial position, by locking means, and further, the double ended needle assembly 10 can be movably pushed to the second position by unlocking the lock by unlocking means.

According to claim 2 of the present invention, in the syringe device according to claim 1, a projected piece 51 for locking the intermediate holder 3 at the standby position in abutment against an edge in a longitudinal direction of the first cylindrical part 11 as the locking means is disposed in the intermediate holder 3, and further, a guide groove 34 serving as the unlocking means, which movably guides the intermediate holder 3 from the standby position toward the partition wall by the fitting of the projected piece 51 owing to the turn of the intermediate holder 3, is formed at the first cylindrical part 11.

According to claim 3 of the present invention, a method of preparing liquids and solutions by using the syringe device according to claim 1 or claim 2 of the present invention comprises the steps of: inserting and pushing a push rod 15 into a first syringe 1, so as to unseal a tip of a bottom of the first syringe 1 with one needle sharp tip 55*b* of a double ended needle assembly 10; pushing an intermediate holder 3 inside of a first cylindrical part 11 toward a partition wall 31, so as to unseal a tip of a bottom of a second syringe 2 with the other needle sharp tip 55*a* of the double ended needle assembly 10; and alternately pushing the push rod 15 and another push rod 16 inserted into the syringes 1 and 2, respectively, in the state in which both of the syringes 1 and 2 communicate with each other via the double ended needle assembly 10, so as to mix and dissolve a solution with and in a pharmaceutical drug, thus producing the liquids and solutions.

Eefects of the Invention (1) The predetermined positional interrelationship among the first syringe containing the solution therein, the second syringe containing the soluble pharmaceutical drug such as a solid lyophilized product or a powdery agent therein, and the double ended needle assembly for allowing the first and second syringes to communicate with each other is held by the single connecting holder. In this held state, the solution is mixed with and dissolved in the pharmaceutical drug. Thus, the solution can be readily mixed with and dissolved in the pharmaceutical drug while the predetermined positional interrelationship among both of the syringes and the double ended needle assembly can be stably held even by an inexperienced person, unlike the prior art shown in FIGS. 18 and 19, in which the outside syringe pierces the vial, and then, the pressure reducing syringe is inserted into the outside syringe, followed by mixing and dissolving.

(2) The solution and the lyophilized product or the like in the predetermined quantity can be mixed with each other while being contained inside of the syringes, respectively. Thus, the liquid medicine can be accurately produced in a desired concentration and quantity, unlike the prior art shown in FIGS. 18 and 19, in which the predetermined quantity of solution is sucked up from the vial based on the visual measurement. In addition, the mixed and dissolved liquid medicine is contained inside of, for example, the first syringe, so that the first syringe and the intermediate holder as they are can be utilized in giving the liquid medicine to a person, thus improving operational efficiency.

(3) The mixture and the dissolution can be performed in the state in which both of the syringes and the double ended needle assembly are contained inside of the connecting holder, thus enhancing operational safety and improving sanitation without any spattering of the liquid medicine outside even if the liquid medicine leaks during the operation.

(4) The operation in the first step, in which there are provided the locking portion for locking the double ended needle assembly inside of the first cylindrical part at the initial position, at which nothing acts on the second syringe, the locking means for locking the intermediate holder inside of the first cylindrical part at the standby position, at which nothing acts on the double ended needle assembly at the initial position, and the unlocking means for the locking means, thus pushing the first syringe into the locked intermediate holder, so as to unseal the first syringe; and the operation in the second step, in which the locking means is unlocked, so that the double ended needle assembly is pushed from the initial position to the second position together with the first syringe and the intermediate holder, so as to unseal the second syringe, thus allowing both of the syringes to communicate with each other, are necessarily performed in this order. Thus, the mixing and dissolving operations can be performed without any mistake of the operational order even by an inexperienced person. Specifically, in the operation in the first step, the first syringe on the side of the solution is unsealed by piercing the first syringe with the needle sharp tip of the double ended needle assembly, so that the first syringe is deaerated. Thereafter, both of the syringes communicate with each other by piercing the second syringe with the needle sharp tip of the double ended needle assembly, followed by mixing and dissolving. Thus, it is possible to prevent any generation of bubbles in the lyophilized product, so as to smoothly dissolve the lyophilized product.

(5) The flange as the locking means is formed at the intermediate holder, and further, the guide groove as the unlocking means is formed at the connecting holder. Thus, the fabrication is easy, and further, the unlocking operation also is easy since the lock can be unlocked only by rotating the intermediate holder.

(6) Since a rib as the locking portion for locking the double ended needle assembly at the initial position is formed at the inner circumferential surface of the first cylindrical portion, the fabrication is easy.

BEST MODE FOR CARRYING OUT THE INVENTION

Figure 10:
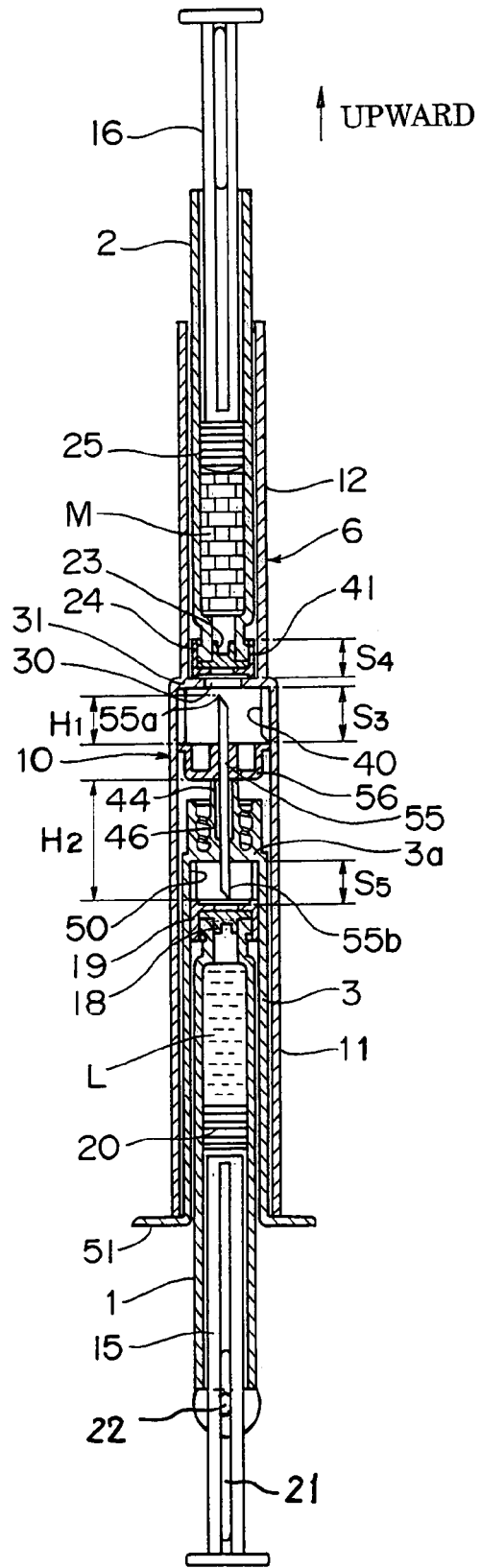
FIG. 10 is a vertically cross-sectional view showing a state immediately before operation in the syringe device, to which the invention is applied.

FIGS. 1 to 17 show an embodiment according to the present invention. A syringe device according to the present invention, as shown in FIG. 10, comprises: a cylindrical connection holder 6 partitioned into a first cylindrical part 11 on a lower side and a second cylindrical part 12 on an upper side via a partition wall 31; a double ended needle assembly 10 and a cylindrical and bottomed intermediate holder 3 which are fitted into the first cylindrical part 11; a first syringe 1 which contains an attached solvent L in a predetermined quantity therein and is inserted into the intermediate holder 3; a second syringe 2 which contains therein a lyophilized product M under a reduced pressure and is inserted into the second cylindrical part 12; and push rods 15 and 16 inserted into the syringes 1 and 2, respectively. In the embodiment, each of the syringes 1 and 2, the intermediate holder 3, the connection holder 6 and the push rods 15 and 16 is made of a transparent glass material, but may be made of plastic or other opaque materials. Although in the above description, the side of the second cylindrical part 12 and the side of the first cylindrical part 11 in the connection holder 6 are referred to as "the upper side" and "the lower side", respectively, they are defined merely for the sake of explanation, and therefore, the embodiment is not limited to the vertical relationship.

Figure 1:
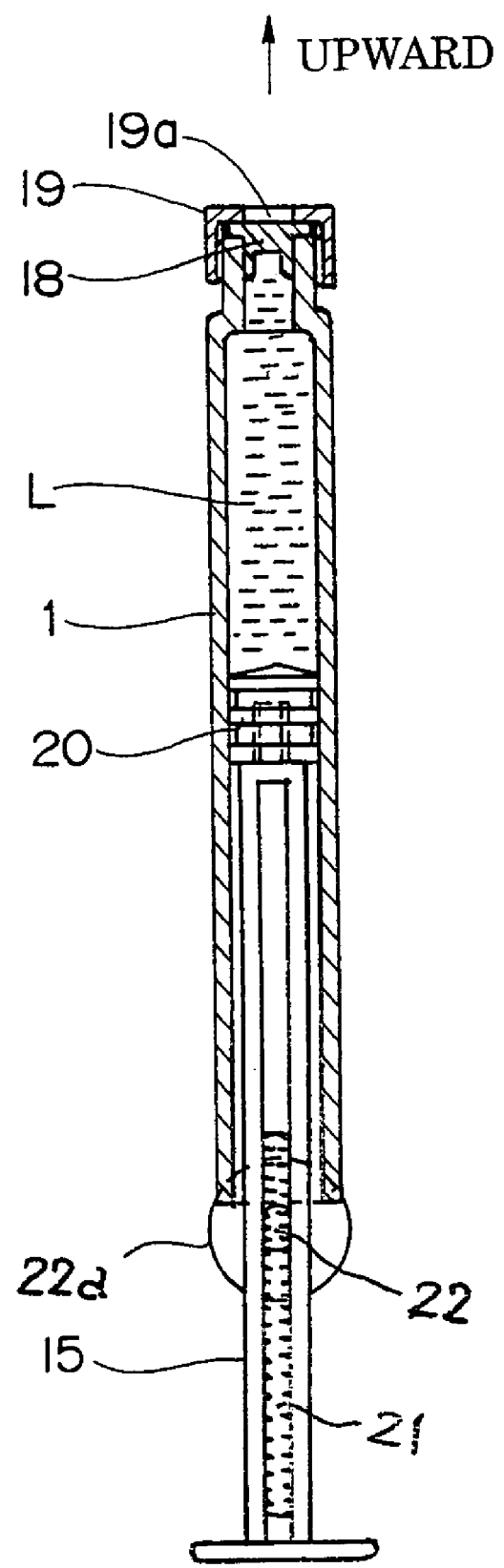
FIG. 1 is a vertically cross-sectional view showing a first syringe in a syringe device, to which the invention is applied.

FIG. 1 is a vertically cross-sectional view showing the first syringe 1 for the solution. The first syringe 1 is formed into a bottomed cylindrical shape and is sealed by an unsealable rubber packing 18 at an upper bottom thereof. The rubber packing 18 is secured via a plastic cap 19 fitted at the upper end of the first syringe 1. A center hole 19a for inserting a needle therethrough is formed in the cap 19. The attached solvent L is contained in a predetermined quantity inside of the first syringe 1. A lower surface of the first syringe 1 containing the attached solvent L therein is sealed by a rubber piston (i.e., a gasket) 20 which is slidably fitted into the first syringe 1. A tip (i.e., an upper end) of the push rod 15 is screwed to the piston 20. A stopper fitting hole 21 which greatly extends in a longitudinal direction of the rod 15 is formed in the push rod 15. A stopper 22 is fitted into the stopper fitting hole 21 in a withdrawable manner at an arbitrary position in the longitudinal direction of the rod 15. When the stopper 22 is fitted to a lower edge of the first syringe 1, the push rod 15 can be prevented from being pushed into the first syringe 1 from a desired position.

Figure 8:
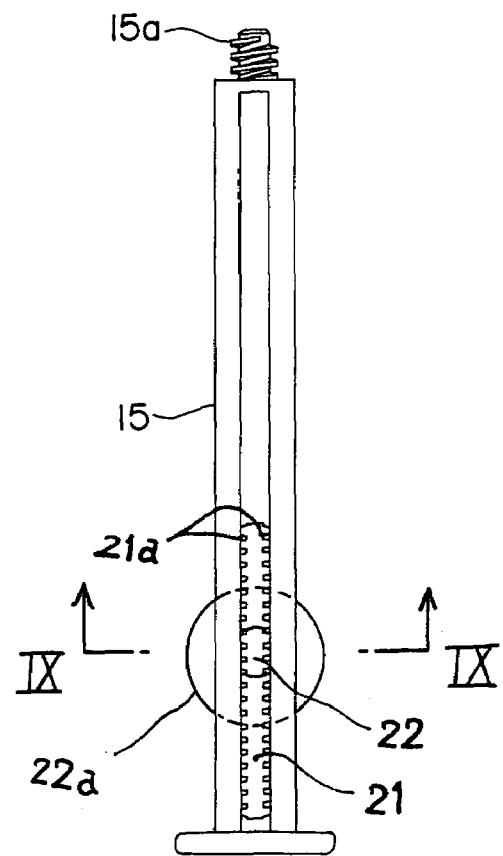
FIG. 8 is a front view showing a push rod in the syringe device, to which the invention is applied.
Figure 9:
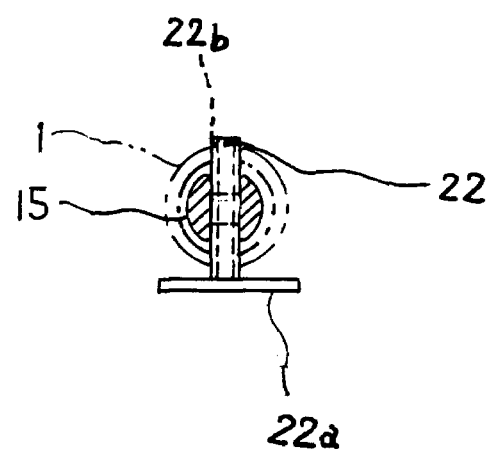
FIG. 9 is a cross-sectional view showing the push rod, taken along a line IX-IX of FIG. 8.

FIG. 8 is an enlarged view showing the push rod 15. Numerous locking projections 21a are formed at the inner circumferential surface of the stopper fitting hole 21 at equal intervals in a vertical direction. As shown in a cross-sectional view, FIG. 9, a plurality of recesses 22b to be fitted to the projections 21a, respectively, are formed at the stopper 22. The engagement of the projection 21a with the recess 22b inhibits any movement in the longitudinal direction of the rod. Furthermore, a flange 22a is formed at an end of the stopper 22. The stopper 22 has the function of preventing any leakage of the attached solvent L if the push rod 15 is pushed into the first syringe 1 at the time of, principally, shipment, carriage and transportation. Incidentally, the push rod 16 on the upper side in FIG. 10 also is constituted in the same manner as the push rod 15 on the lower side except that the push rod 16 does not particularly include any stopper like the stopper 22 of the push rod 15.

Figure 2:
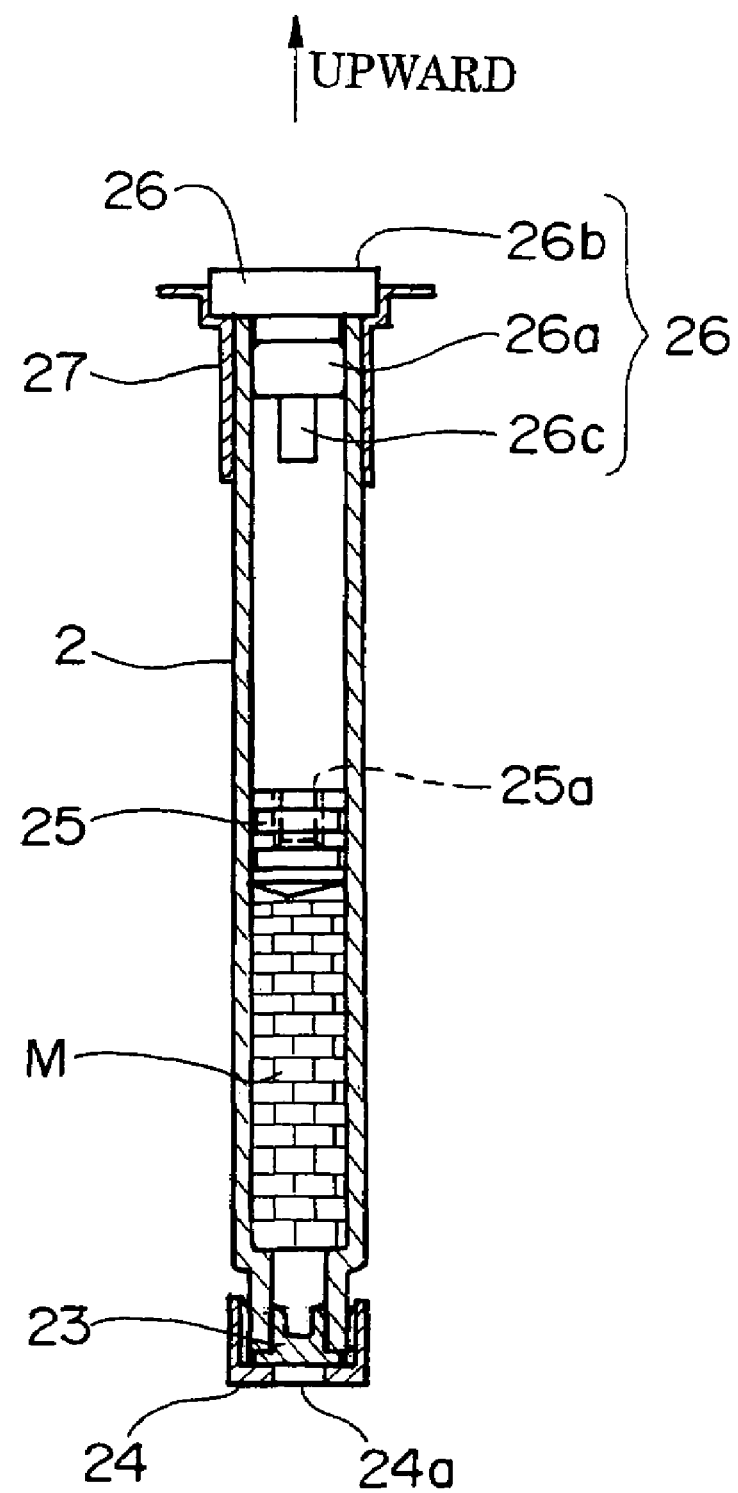
FIG. 2 is a vertically cross-sectional view showing a second syringe in the syringe device, to which the invention is applied.

FIG. 2 is a vertically cross-sectional view showing the second syringe 2 for the lyophilized product at the time of the shipment. The second syringe 2 is formed into a bottomed cylindrical shape. A lower bottom of the second syringe 2 is sealed by an unsealable rubber packing 23, which is secured via a plastic cap 24 fitted at the lower end of the second syringe 2. A center hole 24a for inserting a needle therethrough is formed at the cap 24. Here, component parts for the second syringe 2, the rubber packing 23 and the cap 24 are identical to those for the first syringe 1, the rubber packing 18 and the cap 19 shown in FIG. 1, respectively. With reference to FIG. 2 again, the lyophilized product M is contained under a reduced pressure inside of the second syringe 2. A rubber piston 25 is slidably fitted at an upper inner surface of the second syringe 2 containing the lyophilized product M therein. A female screw 25a for connecting the push rod is formed on the piston 25. A sealed rubber plug 26 is fitted in upper opening of the second syringe 2 and includes a large-diameter body 26a for maintaining an air-tight state in press-contact with the inner circumferential surface of the second syringe 2, a flange 26b to be locked at an upper edge of the second syringe 2, and a small-diameter projection 26c projecting downward from the body 26a. The projection 26c is set in a dimension enough to be slightly press-fitted to the female screw 25a at the piston 25, and therefore, cannot fall during production of the lyophilized product. Furthermore, a cylindrical half hammering plug jig 27 for use in a sealing process under a reduced pressure around the second syringe 2 at the upper end thereof remains in a fitted state.

Figure 3:
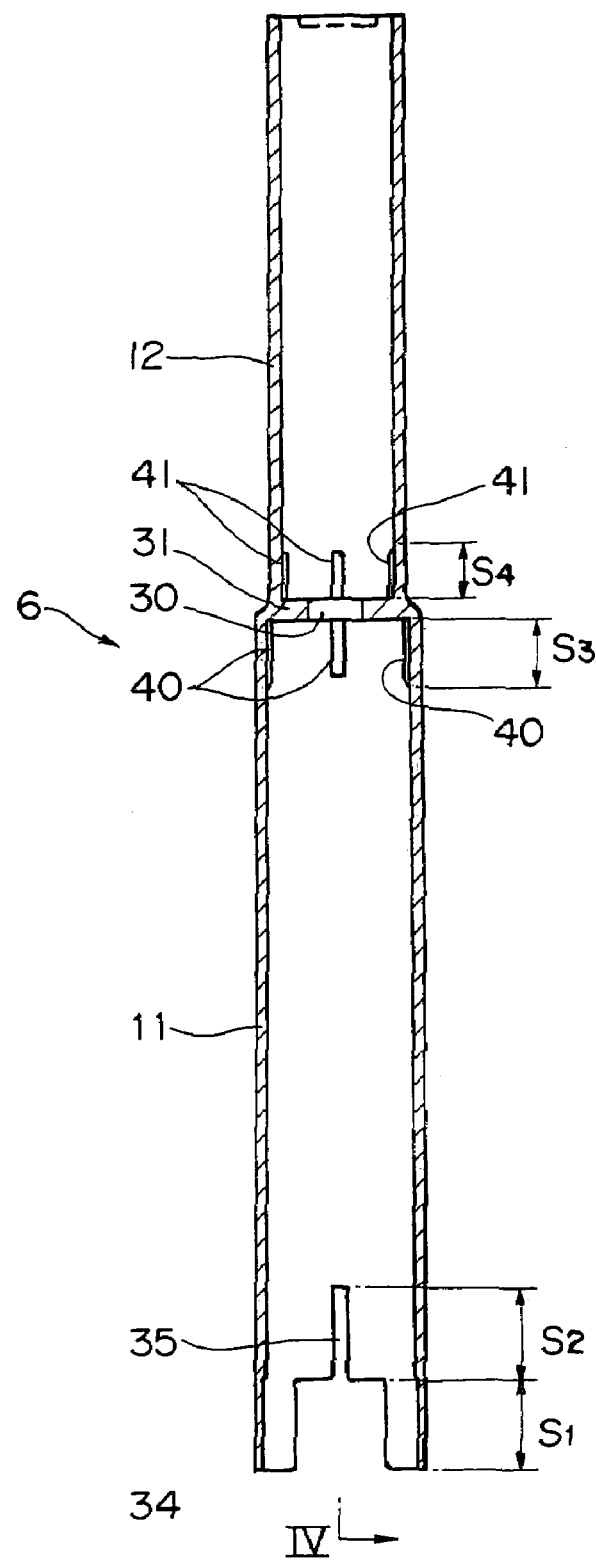
FIG. 3 is a vertically cross-sectional view showing a connection holder in the syringe device, to which the invention is applied.

FIG. 3 is a vertically cross-sectional view showing the connection holder 6. A partition wall 31 is formed at the middle in a longitudinal direction and has a communication hole 30. The connection holder 6 is partitioned into the large-diameter first cylindrical part 11 for fitting the intermediate holder disposed under and the small-diameter second cylindrical part 12 for fitting the second syringe disposed above on the boundary of the partition wall 31.

A guide groove 34 serving as unlocking means in a predetermined vertical length (i.e., a depth) S1 is formed at the lower end of the first cylindrical part 11. Moreover, a slit-like sub guide groove 35 extending upward more by a predetermined length S2 is formed at the upper end of the guide groove 34.

A plurality of locking ribs 40 and a plurality of locking ribs 41 are formed on the inner circumferential surface of the connection holder 6. The locking ribs 40 serve as locking portions for the double ended needle assembly and extend downward by a predetermined length S3 from a lower surface of the partition wall 31. The locking ribs 41 serve as locking portions for the second syringe and extend upward by a predetermined length S4 from an upper surface of the partition wall 31. The locking ribs 40 and 41 are formed at equal intervals in the number of four each in the circumferential direction.

Figure 4:
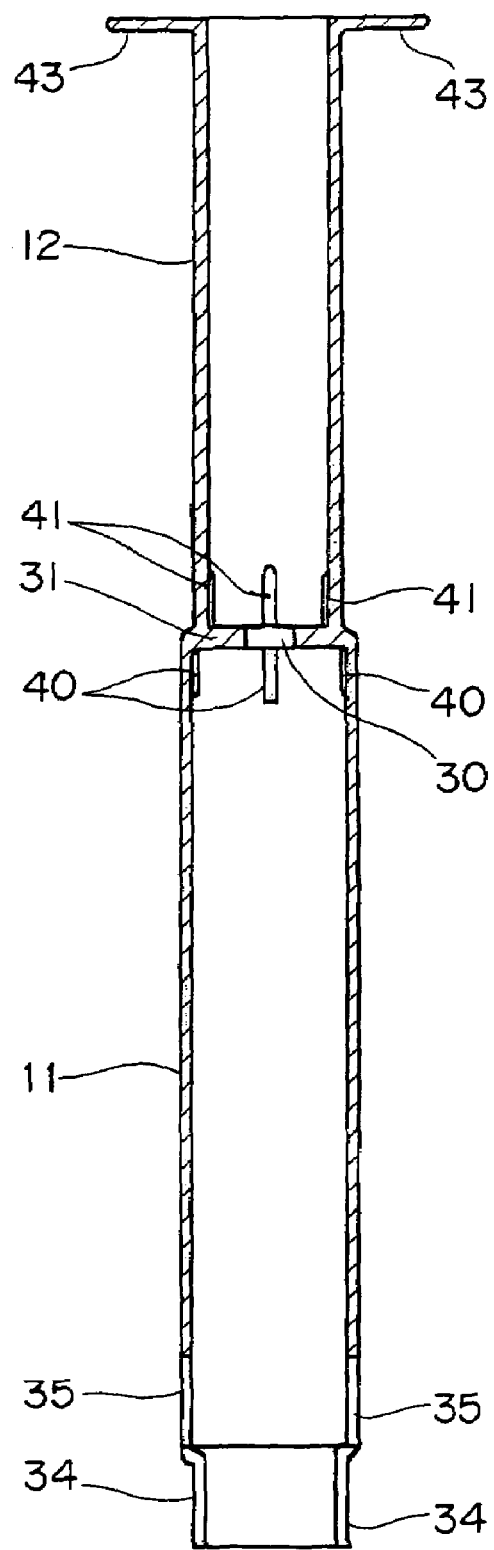
FIG. 4 is a cross-sectional view showing the connection holder, taken along a line IV-IV of FIG. 3.

FIG. 4 is a cross-sectional view taken along a line IV-IV of FIG. 3. The guide grooves 34 formed at the lower end of the first cylindrical part 11 are paired at an interval of 180° in the circumferential direction. A pair of finger gripping flanges 43 are formed outward at an interval of 180° in the circumferential direction at the upper end of the second cylindrical part 12.

Figure 5:
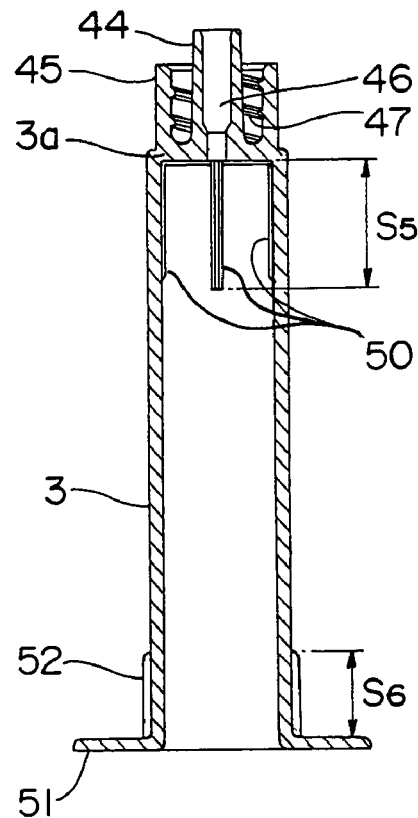
FIG. 5 is a vertically cross-sectional view showing an intermediate holder in the syringe device, to which the invention is applied.

FIG. 5 is a vertically cross-sectional view showing the intermediate holder 3. An inner cylindrical portion 44 for inserting a needle therethrough and an outer cylindrical portion 45 for fitting a needle thereto are formed on an upper bottom 3a of the intermediate holder 3 and they project upward. A needle inserting hole 46 penetrating in a vertical direction is formed at the inner cylindrical portion 44. In the meantime, a spiral groove 47 for holding a needle therein at the inner circumferential surface of the outer cylindrical portion 45. A plurality of locking ribs 50 for the first syringe are formed on the inner circumferential surface of the intermediate holder 3 and extend downward from the upper bottom 3a by a predetermined length S5. A pair of finger hooking projected pieces 51 extending outward in a radial direction are integrally formed on the lower end of the intermediate holder 3. Moreover, a pair of ribs 52 extending upward from the finger hooking projected pieces 51 by a predetermined length S6 at the outer peripheral surface of the intermediate holder 3.

Figure 6:
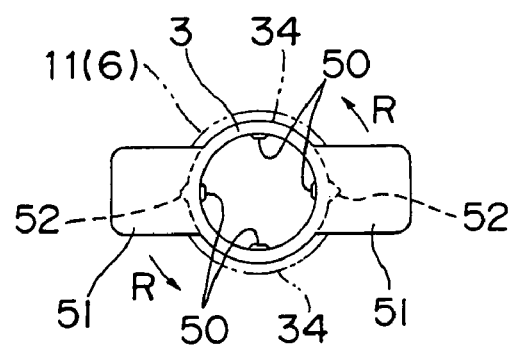
FIG. 6 is a bottom view showing the intermediate holder shown in FIG. 5.

FIG. 6 is a bottom view of FIG. 5. The locking ribs 50 formed at the inner circumferential surface of the intermediate holder 3 are arranged at equal intervals in the number of four in the circumferential direction. The finger hooking projected piece 51 and the ribs 52 each are paired at an interval of 180° in the circumferential direction. Here, a circumferential width of the finger hooking projected 51 is set to a dimension enough to be fitted into the guide groove 34 at the connection holder 6 (indicated by a virtual line). In the meantime, the rib 52 is set to a dimension enough to be fitted into the sub guide groove 35 shown in FIG. 3.

Figure 7:
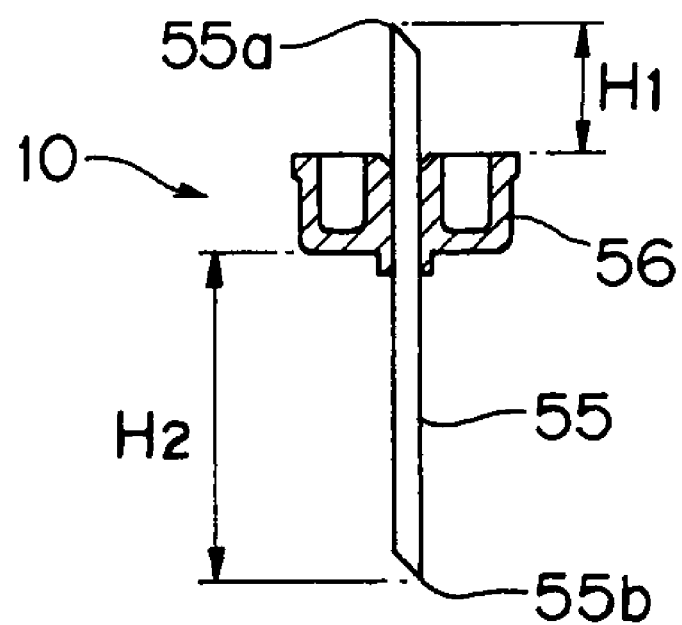
FIG. 7 is a vertically cross-sectional view showing a double ended needle assembly in the syringe device, to which the invention is applied.

FIG. 7 is a vertically cross-sectional view showing the double ended needle assembly 10. The double ended needle assembly 10 is constituted of a plastic needle holder 56 formed into a bottomed cylindrical shape and a double ended needle 55 securely fixed to the center of the needle holder 56. Sharp ends 55a and 55b acutely cut off are formed at openings at both of upper and lower ends of the double ended needle 55. A needle projecting length H1 upward from the needle holder 56 and a needle projecting length H2 downward from the needle holder 56 need be set enough to penetrate the rubber packings 23 and 18 shown in FIG. 10, respectively, but not to interfere with the pistons 25 and 20, respectively. The description will be made later in greater detail under the section of an assembled state.

[Assembled State of Syringe Device Immediately Before Use]

FIG. 10 shows an assembled state of the syringe device immediately before use. Before use, the intermediate holder 3, the double ended needle assembly 10 and the first syringe 1 are incorporated in the connection holder 6: in contrast, the second syringe 2 for the lyophilized product is provided while including the sealed rubber plug 26 and the half hammering plug jig 27, as shown in FIG. 2. The sealed rubber plug 26 is detached from the second syringe 2 immediately before use, and then, the second syringe 2 is inserted into the second cylindrical part 12 of the connection holder 6, as shown in FIG. 10.

The second syringe 2 inserted into the second cylindrical part 12 is stably secured inside of the second cylindrical part 12 at a final insertion stroke (S4) by pushing the cap 24 to the partition wall 31 against the frictional resistance of the locking rib 41. In the meantime, the double ended needle assembly 10 and the intermediate holder 3 are inserted into the first cylindrical part 11 in this order, wherein the first syringe 1 containing the attached solvent L therein is inserted into the intermediate holder 3. The push rods 15 and 16 are screwed, respectively, in the respective pistons 20 and 25 inside of the first and second syringes 1 and 2. In this stage, even if the stopper 22 for the push rod 15 is detached, the following operation can be substantially implemented enough to be smoothly performed. However, the stopper 22 remains disposed in order to securely prevent any leakage of the attached solvent L by an accidental operation.

The double ended needle assembly 10 is stopped at an initial position apart by the predetermined distance (i.e., the length of the rib) S3 from the partition wall 31 since the upper end of the needle holder 56 is locked by the locking ribs 40 inside of the first cylindrical part 11. The upward projecting length H1 of the double ended needle 55 is set to be smaller than the length S3 of the locking ribs 40. As a consequence, the upper sharp tip 55a of the double ended needle 55 does not project inward of the second syringe 2 at the initial position of the double ended needle assembly 10, and therefore, does not pierce the rubber packing 23 of the second syringe 2. Incidentally, in the present embodiment, the upper sharp tip 55a is located under the partition wall 31.

The intermediate holder 3 is inserted to the standby position, at which the finger hooking projected piece 51 at the lower end abuts against the lower edge of the first cylindrical part 11. At this standby position, the downward projecting portion of the double ended needle 55 is inserted into the needle inserting hole 46 of the intermediate holder 3, so that the upper end of the inner cylindrical portion 44 is brought into slight contact with the lower surface of the needle holder 56 or comes very close to the lower surface of the needle holder 56.

The first syringe 1 inserted into the intermediate holder 3 is stopped at a position apart by the distance S5 from the upper bottom 3a of the intermediate holder 3 since the upper cap 19 is locked in the locking rib 50 at the upper end inside of the intermediate holder 3. Thus, the lower sharp tip 55b of the double ended needle 55 does not pierce the rubber cap 18 in the first syringe 1.

[Production of Lyophilized Product and Sealing Method under Reduced Pressure]

Figure 16:
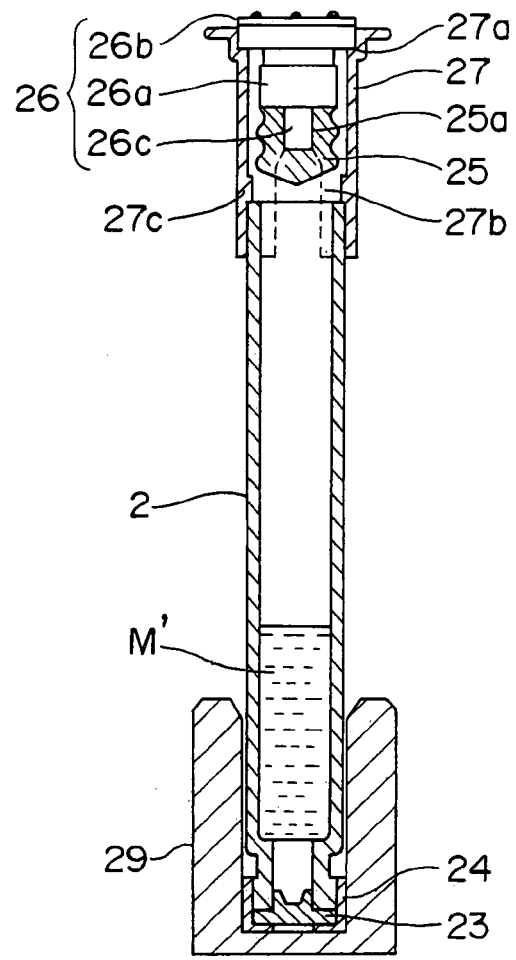
FIG. 16 is a vertically cross-sectional view showing the second syringe in a method for sealing a lyophilized product into the second syringe under a reduced pressure.
Figure 17:
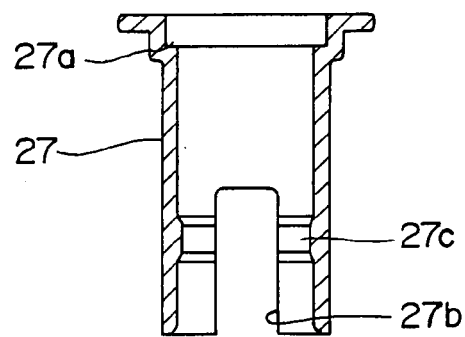
FIG. 17 is a vertically cross-sectional view showing a half hammering plug jig shown in FIG. 16 in enlargement.

Next, before explanation is made on operation for mixing and dissolving the lyophilized product, a description will be simply given of the structure of the half hammering plug jig 27 (see FIG. 2) and a method for producing the lyophilized product M inside of the second syringe 2 and sealing it under a reduced pressure in reference to FIGS. 16 and 17.

FIG. 17 is a vertically cross-sectional view showing the half hammering plug jig 27 in enlargement. A flange and an annular step 27a for allowing the sealed rubber plug to be seated thereon are formed at the upper end of the half hammering plug jig 27. An air-liquid relieving groove 27b for use in a pressure reducing process is formed at a lower half portion of the half hammering plug jig 27. Furthermore, an inward locking projection 27c for locking the half hammering plug jig 27 at a position of a half hammering plug is formed at the inner circumferential surface.

FIG. 16 shows the process for producing the lyophilized product. The second syringe 2 having the rubber packing 23 and the cap 24 disposed thereat is upright held on a cylindrical support mount 29. A liquid medicine M' before being frozen and dried is contained inside of the second syringe 2 in the held state, the half hammering plug jig 27 is fitted around the upper end of the second syringe 2, and then, the inward locking projection 27c is locked at the upper edge of the second syringe 2, which is thus stopped at the position of the half hammering plug. The female screw 25a of the piston 25 is fitted to the projection 26c of the sealed rubber plug 26, and thereafter, the sealed rubber plug 26 is inserted into the half hammering plug jig 27 from above. As a consequence, the flange 26b of the sealed rubber plug 26 is seated at the annular step 27a of the half hammering plug jig 27.

The second syringe 2 in the half hammering plug state, as shown in FIG. 16, is put into a freeze-drier, thereby freezing the liquid medicine M', followed by removing moisture or the like under a reduced pressure inside of the freeze-drier. The removed moisture is relieved to the outside through the air-liquid relieving groove 27b formed at the half hammering plug jig 27. After the relief of the moisture or the like, the sealed rubber plug 26 together with the half hammering plug jig 27 is pushed down to a fully hammering plug position, at which the flange 26b is locked at the upper edge of the second syringe 2, to be thus sealed under the reduced pressure.

[Operation for Mixing Attached Solvent and Dissolving]

(1) Operation in First Stage

Figure 11:
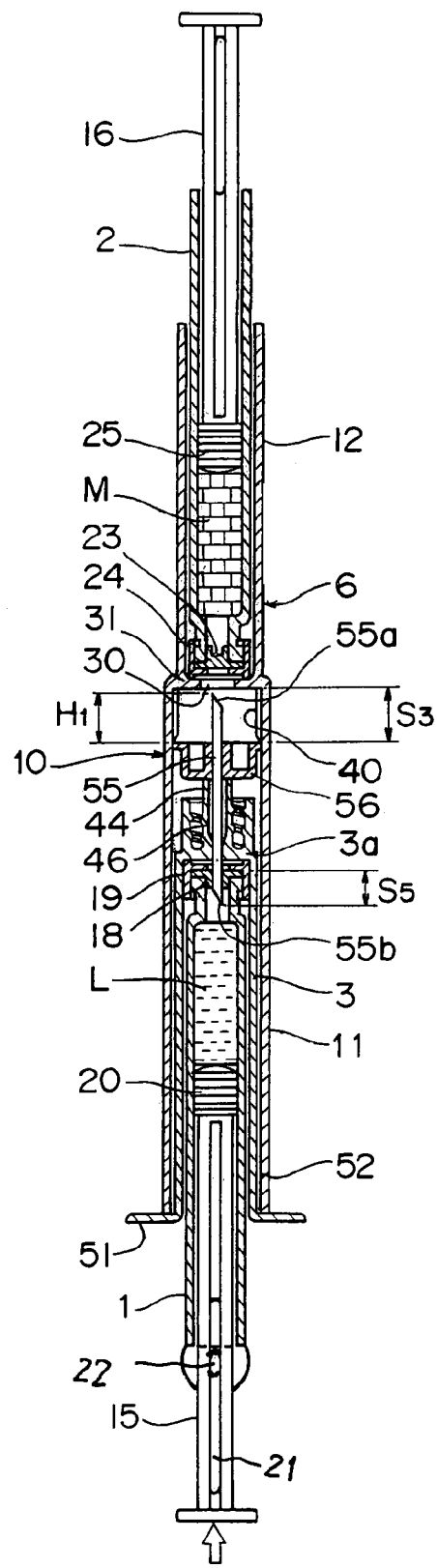
FIG. 11 is a vertically cross-sectional view showing an operational state in a first stage in the syringe device, to which the invention is applied.

In FIG. 10, the connection holder 6 is held by one hand of an operator while the push rod 15 on the side of the first syringe 1 is pushed by the other hand of the operator. For example, the index and middle fingers of one hand hook on the finger hooking projected pieces 51 of the intermediate holder 3, and further, a thumb pushes the push rod 15. Consequently, the first syringe 1 is moved upward with respect to the intermediate holder 3 via the stopper 22 together with the push rod 15 against the frictional resistance of the locking rib 50, and thereafter, the cap 19 comes to a halt in abutment against the upper bottom 3a of the intermediate holder 3 at a timing when the first syringe 1 is moved upward by the distance S5, as shown in FIG. 11. The first syringe 1 is moved by the distance S5 with respect to the intermediate holder 3, so that the lower sharp tip 55b of the double ended needle 55 pierces the rubber cap 18 in the first syringe 1, thereby unsealing the first syringe 1. In this manner, the first syringe 1 is deaerated by unsealing the first syringe 1 in the operation in the first stage. Since the double ended needle assembly 10 is held at the initial position by the locking ribs 40 inside of the first cylindrical part 11 during the operation in the first stage, the double ended needle assembly 10 cannot be moved upward, and further, the intermediate holder 3 cannot be moved upward since the finger hooking projected piece 51 is locked to the lower edge of the first chamber 11, so that the second syringe 2 cannot be unsealed. Additionally, the rib 52 formed at the outer peripheral surface of the intermediate holder 3 is brought into press-contact with the inner circumferential surface of the first cylindrical part 11, and therefore, the intermediate holder 3 can be stably held in the first cylindrical part 11 without any play in a radial direction.

(2) Operation in Second Stage

After the first syringe 1 is unsealed, as described above, the intermediate holder 3 is rotated at an angle of 90° thereon, as indicated by an arrow R in FIG. 6, from the state shown in FIG. 11, so that the finger hooking projected piece 51 mates with the guide groove 34, in an operation in a second stage. Specifically, the intermediate holder 3 is unlocked at the standby position, and thus, the finger hooking projected piece 51 can be moved upward inside of the guide groove 34. Thereafter, the intermediate holder 3 is pushed upward from the standby position shown in FIG. 11, so that the double ended needle assembly 10 is moved by the distance S3 from the initial position shown in FIG. 11 to a second position shown in FIG. 12 against the frictional resistance of the locking ribs 40. The movement of the double ended needle assembly 10 by the distance S3 allows the upper sharp tip 55a of the double ended needle 55 to pass through the through hole 30 formed on the partition wall 31, and then, to project inward of the second cylindrical part 12, so as to pierce the rubber packing 23 of the second syringe 2, thus unsealing the second syringe 2. As a consequence, the first and second syringes 1 and 2 communicate with each other via the double ended needle 55.

Here in the operation in the second stage, at the same time when the finger hooking projected piece 51 at the intermediate holder 3 is moved upward inside of the guide groove 34, the upper rib 52 of the finger hooking projected piece 51 is moved upward inside of the sub guide groove 35. Moreover, after the operation in the second stage, the stopper 22 of the push rod 15 of the first syringe 1 is detached.

(3) Operation in Third Stage

Figure 12:
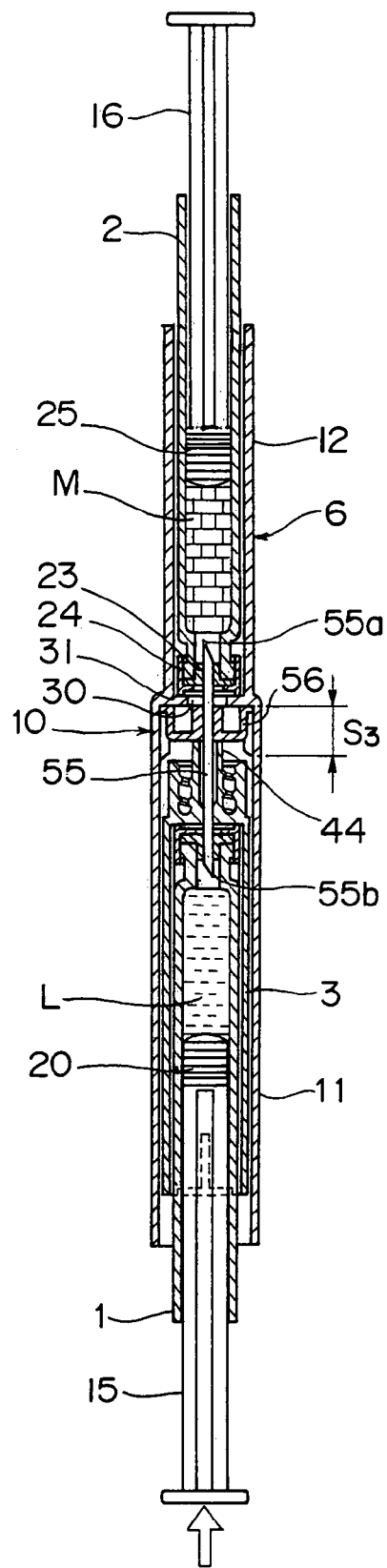
FIG. 12 is a vertically cross-sectional view showing an operational state in a second stage in the syringe device, to which the invention is applied.
Figure 13:
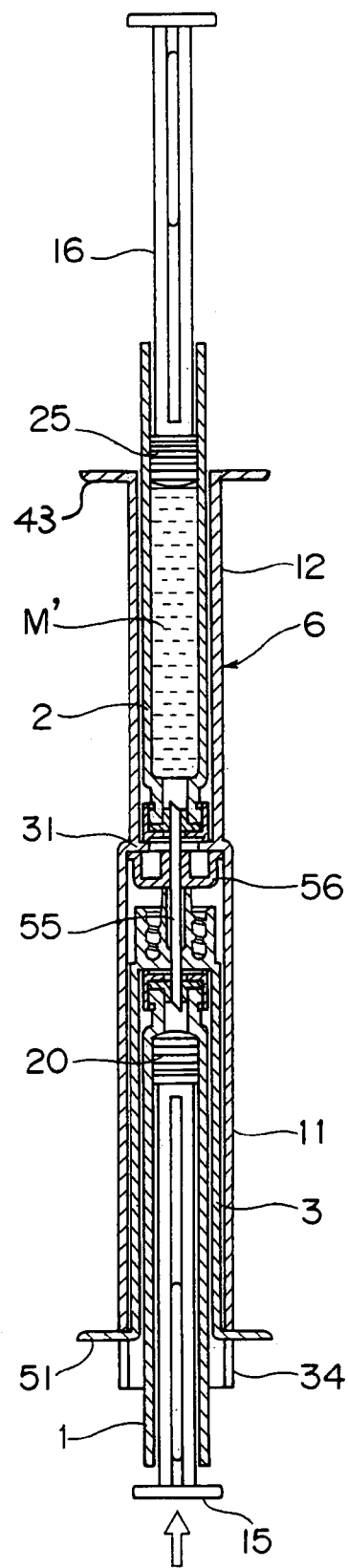
FIG. 13 is a vertically cross-sectional view showing a state in which a solution is injected into the second syringe in the syringe device, to which the invention is applied.

As shown in FIG. 12, the push rod 15 of the first syringe 1 is operated by one hand of an operator while the push rod 16 of the second syringe 2 is operated by the other hand of the operator in the state in which the first and second syringes 1 and 2 communicate with each other, thereby mixing the attached solvent L with the lyophilized product M, and further, strongly agitating them, followed by speedy dissolution. For example, the index and middle fingers of one hand hook on the finger hooking projected piece 51 of the intermediate holder 3, and further, the thumb pushes the push rod 15. Moreover, the index and middle fingers of the other hand hook on the finger gripping flange 43 at the upper end of the connection holder 6, and further, the thumb pushes the push rod 16. Thus, as shown in FIGS. 13 and 14, both of the push rods 15 and 16 are alternately pushed, thereby mixing the attached solvent L with the lyophilized product M, dissolving the lyophilized product M in the attached solvent L, and producing the liquids and solutions (i.e., the liquid medicine) M'.

(4) Giving Stage

Figure 14:
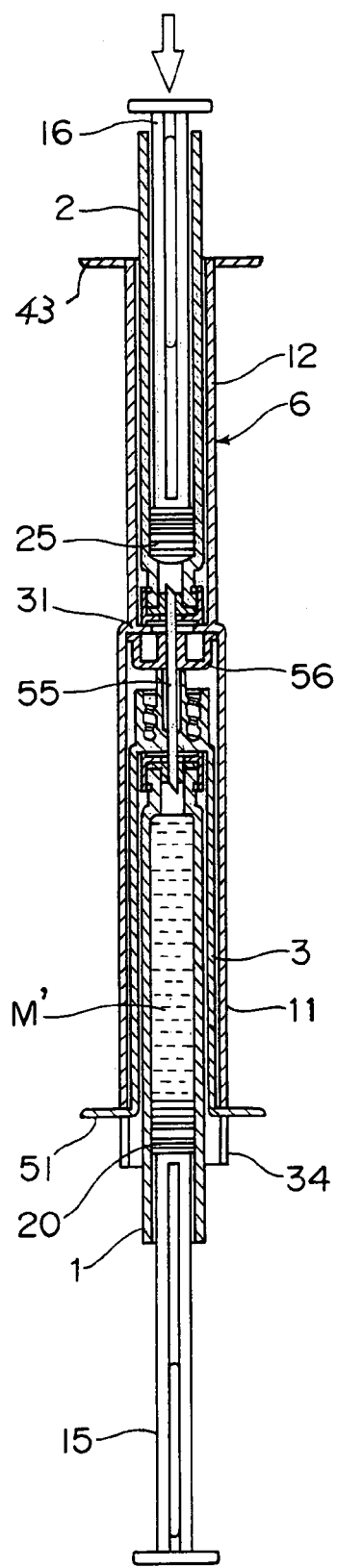
FIG. 14 is a vertically cross-sectional view showing a state in which a mixed liquid medicine is transferred into the first syringe in the syringe device, to which the invention is applied.
Figure 15:
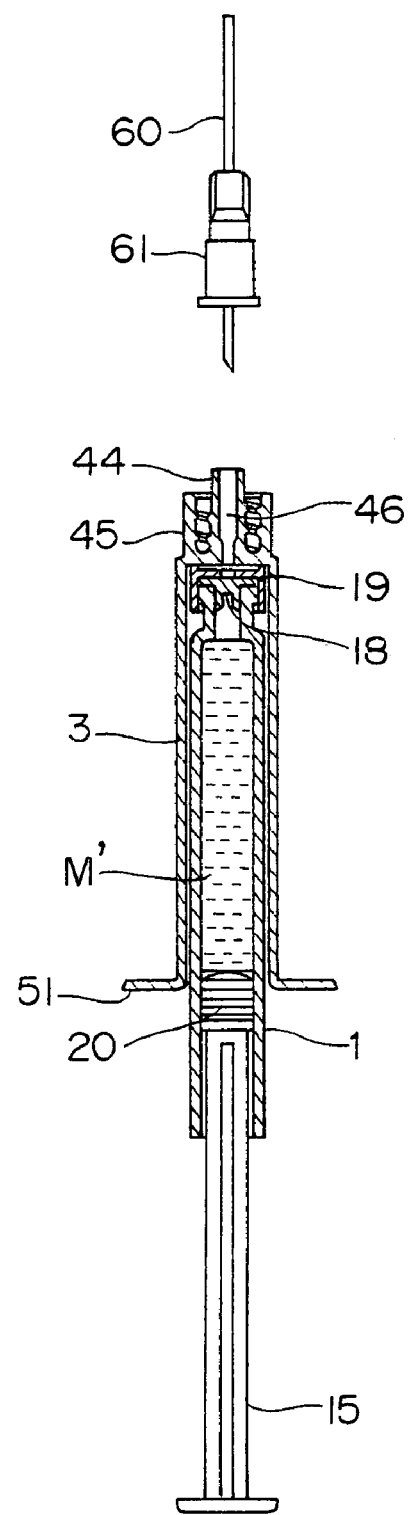
FIG. 15 is a vertically cross-sectional view showing a state in which the liquid medicine after mixture and dissolution is given by the first syringe.

After the production of the liquids and solutions M', all of the liquids and solutions M' is contained in the first syringe 1, as shown in FIG. 14, and then, the first syringe 1 is withdrawn from the first cylindrical part 11 together with the intermediate holder 3. And then, as shown in FIG. 15, a holder 61 of a special-purpose needle 60 is inserted into the outer cylindrical portion 45 at the upper end of the intermediate holder 3, and further, the other end of the special-purpose needle 60 pierces the rubber packing 18, thereby unsealing the first syringe 1 again. As a consequence, the first syringe 1 serving as a syringe gives the liquid medicine.

[Effects which Mode Carrying Out Invention Produces]

Figure 18:
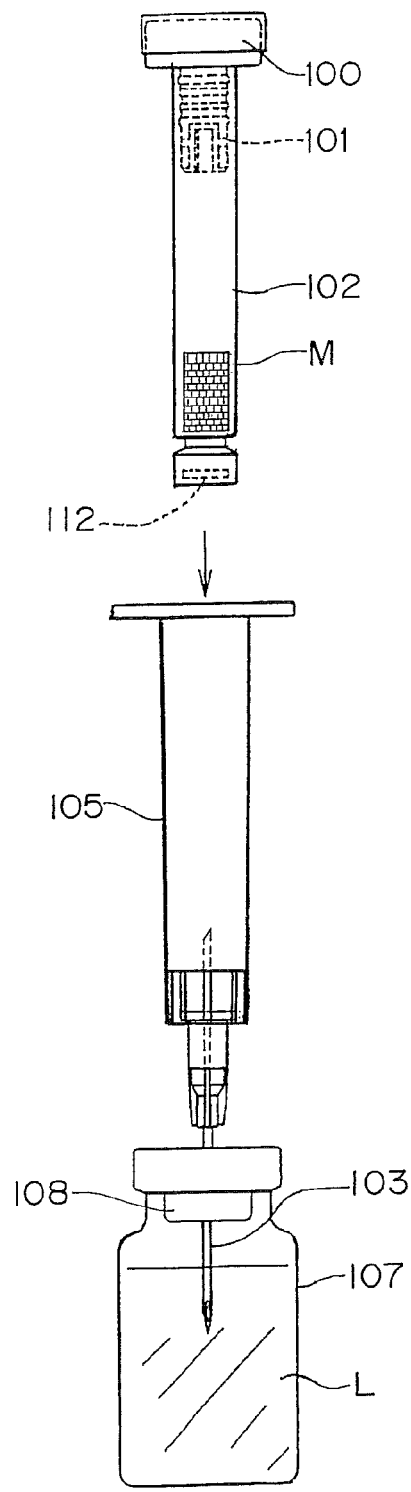
FIG. 18 is a vertically cross-sectional view showing a syringe device in the prior art.
Figure 19:
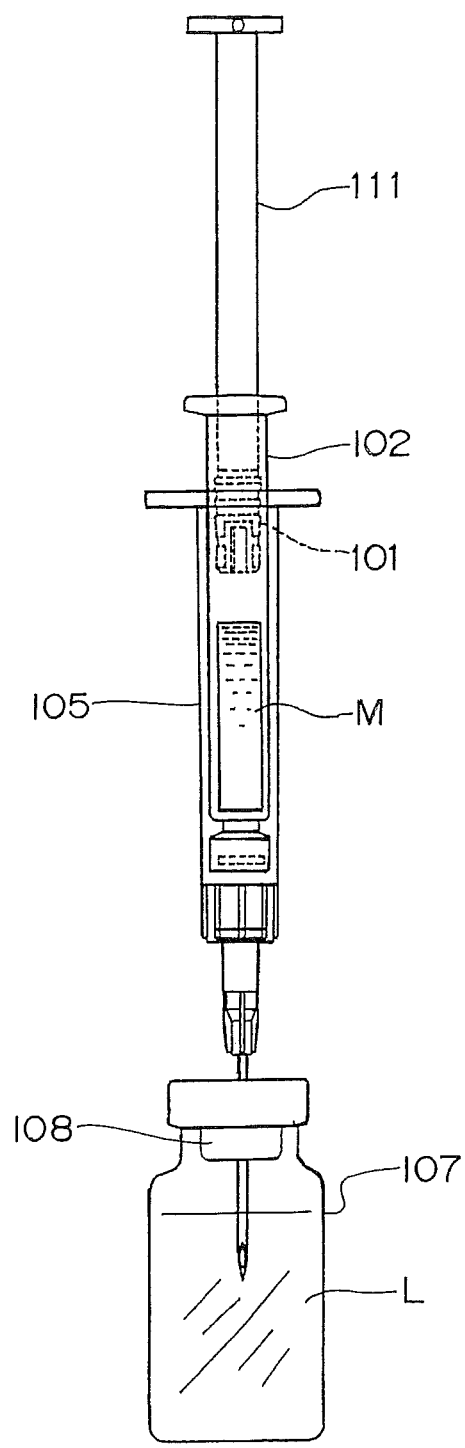
FIG. 19 is a vertically cross-sectional view showing a state during mixing and dissolving operations in the prior art shown in FIG. 18.

(1) According to the carrying-out mode, as shown in FIGS. 13 and 14, in the state in which the second syringe 2 containing the lyophilized product M therein, the first syringe 1 containing the attached solvent L therein, and the double ended needle assembly 10 for allowing both of the first and second syringes 1 and 2 to communicate with each other are held in the predetermined positional interrelationship by the single connection holder 6, the attached solvent L can be mixed with and dissolved in the lyophilized product M. Thus, the mixture and dissolution can be readily implemented while the predetermined positional interrelationship among both of the syringes 1 and 2 and the double ended needle assembly 10 can be stably held even by an inexperienced person, unlike the prior art in which the solution is sucked up from the vial, as shown in FIGS. 18 and 19.

(2) The attached solvent L is mixed with and dissolved in the lyophilized product M by the use of the first syringe 1 containing the predetermined quantity of attached solvent L therein and the second syringe 2 containing the predetermined quantity of lyophilized product M therein. Thus, the liquid medicine can be accurately produced in the predetermined concentration and quantity, unlike the prior art, in which the predetermined quantity of solution is sucked up from the vial based on the visual measurement, as shown in FIG. 19.

(3) The mixture and the dissolution can be performed in the state in which all of the syringes 1 and 2 and the double ended needle assembly 10 are contained inside of the connection holder 6, thus enhancing operational safety and improving sanitation without any spattering of the liquid medicine outside even if the liquid medicine leaks from the syringe during the operation. In addition, the mixed and dissolved liquid medicine M' is contained inside of the first syringe 1, so that the first syringe 1 and the intermediate holder 3 serving as the syringe as they are can be utilized in giving the liquid medicine to a person, thus enhancing operational efficiency.

(4) The operation in the first step, in which there are provided the locking ribs 40 for locking the double ended needle assembly 10 inside of the first cylindrical part 11 at the initial position, at which nothing acts on the second syringe 2, the locking means (i.e., the finger hooking projected piece 51) for locking the intermediate holder 3 inside of the first cylindrical part 11 at the standby position, at which nothing acts on the double ended needle assembly 10 at the initial position, and the unlocking means (i.e., the guide groove 34) for the locking means, thus pushing the first syringe 1 into the locked intermediate holder 3, so as to unseal the first syringe 1; and the operation in the second step, in which the locking means is unlocked, so that the double ended needle assembly 10 is pushed from the initial position to the second position together with the first syringe 1 and the intermediate holder 3, so as to unseal the second syringe 2, thus allowing both of the syringes 1 and 2 to communicate with each other, are necessarily performed in this order. Thus, the mixing and dissolving operations can be performed without any mistake of the operational order even by an inexperienced person. Specifically, in the operation in the first step, the first syringe 1 on the side of the solution is unsealed by piercing the first syringe with the needle sharp tip 55b of the double ended needle assembly 10, so that the first syringe 1 is deaerated. Thereafter, both of the syringes 1 and 2 communicate with each other by piercing the second syringe 2 with the needle sharp tip 55b of the double ended needle assembly 10, followed by the mixing and dissolving operations. Thus, it is possible to prevent any generation of bubbles in the lyophilized product, so as to smoothly dissolve the lyophilized product.

(5) The finger hooking projected piece 51 having the function of hooking the finger during the operation is formed as the locking means for locking the intermediate holder 3 at the standby position, and further, the guide groove 34 as the unlocking means is formed at the connection holder 6. Thus, the fabrication is easy, and further, the unlocking operation also is easy since the lock can be unlocked only by rotating the intermediate holder 3.

(6) Since the ribs 40 as the means for locking the double ended needle assembly 10 at the initial position are merely formed at the inner circumferential surface of the first cylindrical portion, the fabrication is easy.

INDUSTRIAL APPLICABILITY

Although the syringe device and the method of preparing the liquids and solutions using the device according to the present invention are principally utilized in the fabrication of medical equipment and in a medical industry as a device and method of handling a medical liquids and solutions, they may be utilized in processing liquids and solutions for growing a plant, a study and the like.

The invention claimed is:
1. A syringe device comprising:
    a cylindrical connection holder which is partitioned into a first cylindrical part and a second cylindrical part via a partition wall having a through hole formed thereat;
    a cylindrical and bottomed intermediate holder having a needle inserting hole formed at a tip of a bottom thereof;
    a first cylindrical and bottomed syringe which contains a solution therein and is unsealably sealed at a tip of a bottom thereof;
    a second cylindrical and bottomed syringe which contains a soluble pharmaceutical drug therein and is unsealably sealed at a tip of a bottom thereof; and
    a double ended needle assembly;
    the double ended needle assembly and the intermediate holder being inserted in this order into the first cylindrical part, the first syringe being inserted into the intermediate holder, and the second syringe being inserted into the second cylindrical part;
    wherein the double ended needle assembly is locked at an initial position, at which a needle sharp tip on a side of the partition wall cannot project inward of the second cylindrical part by a locking portion, and further, can be moved against a frictional resistance of the locking portion from the initial position to a second position, at which the needle sharp tip passes through the through hole so as to unseal the tip of the bottom of the second syringe; and
    the intermediate holder is locked at a standby position, at which it cannot act on the double ended needle assembly at the initial position, by locking means, and further, the double ended needle assembly can be movably pushed to the second position by unlocking the lock by unlocking means.

2. A syringe device according to claim 1, wherein a projected piece for locking the intermediate holder at the standby position in abutment against an edge in a longitudinal direction of the first cylindrical part as the locking means is disposed in the intermediate holder, and further, a guide groove serving as the unlocking means, which movably guides the intermediate holder from the standby position toward the partition wall by the fitting of the projected piece owing to the turn of the intermediate holder, is formed at the first cylindrical part.

3. A method of preparing liquids and solutions by using the syringe device according to claim 1, the method comprising the steps of:
    inserting and pushing a push rod into a first syringe, so as to unseal a tip of a bottom of the first syringe with one needle sharp tip of a double ended needle assembly;
    pushing an intermediate holder inside of a first cylindrical part toward a partition wall, so as to unseal a tip of a bottom of a second syringe with the other needle sharp tip of the double ended needle assembly; and
    alternately pushing the push rod and another push rod inserted into the syringes and, respectively, in the state in which both of the syringes and communicate with each other via the double ended needle assembly, so as to mix and dissolve a solution with and in a pharmaceutical drug, thus producing the liquids and solutions.

4. A method of preparing liquids and solutions by using the syringe device according to claim 2, the method comprising the steps of:
    inserting and pushing a push rod into a first syringe, so as to unseal a tip of a bottom of the first syringe with one needle sharp tip of a double ended needle assembly;
    pushing an intermediate holder inside of a first cylindrical part toward a partition wall, so as to unseal a tip of a bottom of a second syringe with the other needle sharp tip of the double ended needle assembly; and
    alternately pushing the push rod and another push rod inserted into the syringes and, respectively, in the state in which both of the syringes and communicate with each other via the double ended needle assembly, so as to mix and dissolve a solution with and in a pharmaceutical drug, thus producing the liquids and solutions.

* * * * *